United States Patent [19]

Blanc et al.

[11] Patent Number: Plant 7,180

[45] Date of Patent: Mar. 6, 1990

[54] CARNATION PLANT NAMES LONNISIO

[75] Inventors: Henri Blanc, Antibes, France; Antonio Di Giorgio; Renato Di Giorgio, both of San Remo, Italy

[73] Assignee: Establissements Barberet et Blanc, La Londe-Les-Maures, France

[21] Appl. No.: 315,025

[22] Filed: Feb. 24, 1989

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and original variety of standard carnation particularly distinguished by its medium sized blooms the petals of which having a very light yellow body color bearing red striations which provide generally a flower of light color bearing a reddish heart due to the close gathering of the inner petals which render the flower with an attractive and pleasing appearance. This plant blooms profusely at recurrent intervals in the Spring, Midseason and Fall blooming seasons and the blooms are carried on strong, upright and rigid stems providing a cut flower length averaging about 78 cm. on a well-branched plant having a total height averaging about 130 cm. at eight months of growth and bearing a moderately abundant quantity of foliage.

1 Drawing Sheet

BACKGROUND OF THE NEW PLANT

Our new carnation cultivar originated as a seedling of a hybrid developed by us at the Di Giorgio nursery in San Remo, Italy, by our crossing two carnation varieties selected from the Di Giorgio carnation collection maintained for breeding purposes. The present seedling was selected by us, from a group resulting from planting seeds of the said hybrid, because in our judgment the floral blooms of this seedling were of a very original coloration which should be propagated and tested with a view to ultimate commercialization. Accordingly, the selected seedling was propagated by means of cuttings at San Remo, Italy and such propagation was carried on through several successive generations which demonstrated to us that the novel characteristics of the selected seedling would hold true from generation to generation and that its homogeneity could be assured for commercialization.

This new plant is now being propagated on a commercial scale at Establissements Barberet et Blanc, Laboratoire de Physiologie Vegetale, 83250 La Londe-Les Maures, France.

DESCRIPTION OF THE DRAWING

Our new carnation variety is illustrated by the accompanying photographic drawing which shows buds and blossoms in several stages of development, the color rendition being as nearly true as as is reasonably possible to obtain by professional photographic procedures.

DESCRIPTION OF THE NEW PLANT

The following is a detailed description of our new standard carnation variety based upon observation of plants grown in greenhouse, as well as outdoors, in the Spring of 1988 at San Remo, Italy. The color renditions stated herein being according to the R.H.S. Colour Chart published by The Royal Horticultural Society of London, England.

THE PLANT

Origin: Seedling.

Parentage:

*Seed parent.*—Variety No. 490.

*Pollen parent.*—Variety No. 647.

Both varieties being unnamed and unpatented are identified in the Di Giorgio breeding records maintained at the nursery office at Via Villetta 41, 18038 San Remo, Italy.

Classification:

*Botanic.*—*Dianthus caryophyllus.*

*Commercial.*—Standard Carnation.

Form: Erect and rigid bush having at least four stems emitted near the ground.

Height: Averages about 130 cm. at eight months of growth.

Main stem length: Less than 15 cm. due to pinching for branch production.

Branching: This plant is well branched.

Foilage:

*Quantity.*—Moderately abundant.

*Number of leaves.*—More than 120.

*Leaf size.*—(At the seventh node) About 12.7 cm. long and about 0.8 cm. wide.

*Leaf shape.*—Generally linear with entire margins.

*Texture.*—Leathery.

*Color.*—Both upper and under sides, 189-A/B.

*Ribs and veins.*—Hardly noticeable.

*Rachis.*—Hardly noticeable.

THE BUD

Size: Medium.

*Diameter.*—Averages about 2 cm.

*Length.*—Averages about 3.5 cm.

Shape: Ovoid.

Rate of opening: Average.

Color of petals: When sepals first divide and when the petals begin to unfurl, the same as at full bloom.

Sepals:

*Number.*—Six or seven.

*Shape.*—Generally avoid with an acuminate apex and joined together at the lower parts.

*Character.*—At the beginning, the sepals are hooded over the bud. They curl back as the flowers open.

*Color.*—Inside, 145-D. Outside, 137-D and 144-C.

*Striae.*—Longitudinal.

Calyx:

*Shape.*—Bell-shaped.

*Size.*—Large.

*Aspect.*—Smooth.

*Splitting.*—The calyx splits very little.

Flower stem:

*Length.*—Averages about 78 cm. when cut at the tenth node.

*Character.*—Erect and rigid.

*Color.*—180-A/B.

THE FLOWER

Blooming habit: Recurrent, blooming profusely during the Spring, Midseason and Fall blooming periods with a tendency to give few blooms in the Fall.

Size of flowers: Medium.

*Diameter.*—Averages about 7 cm.

*Depth.*—Averages about 5.4 cm.

Borne: Singly.

Shape: When bloom first opens, high-centered. When bloom matures, dome-shaped.

Petalage:

*Number of petals.*—Averages about seventy-eight.

*Arrangement.*—Imbricated.

*Form.*—Fan-shaped with rounded edges.

*Texture.*—Leathery.

*Aspect.*—Satiny.

*Color.*—Outer petals: Body—4-C with widely spaced striae of Ruby Red 61-A, and Spiraea Red 63-B. Base—Greenish-white. Inner petals: Body—4-C. Striae—61A and 63-B. Base—Greenish-white.

Petaloids:

*Number.*—Less than ten.

*Size.*—Smaller than the petals.

*Color.*—The same as the petals.

Flower stem:

*Character.*—Upright with good strength.

*Color.*—189-A/B.

Discoloration after full bloom: Very little.

Persistence: The petals stay on the stem until withering.

Fragrance: Strong.

Lasting quality: As a cut flower, at least ten days in vase keeping.

REPRODUCTIVE ORGANS

Stamens:

*Number.*—Nine to fourteen.

*Arrangement.*—Around the ovary.

*Anthers.*—Size: Less than 4 mm. Color: Yellowish.

*Filaments.*—Color: Yellowish.

Pistils:

*Number.*—Two to four.

*Styles.*—Length: About 1.7 cm. Color: Yellowish.

*Stigma.*—Color: Yellowish.

Character of ovaries: Ribbed.

This new carnation variety appears to be entirely original and colorwise incomparable with other known carnation varieties.

We claim:

1. The new and distinctive carnation variety substantially as herein shown and described, particularly characterized by the yellow and red coloration of its medium sized blooms the petals of which have dark red striae on each side which show rather densely on the closely gathered inner petals.

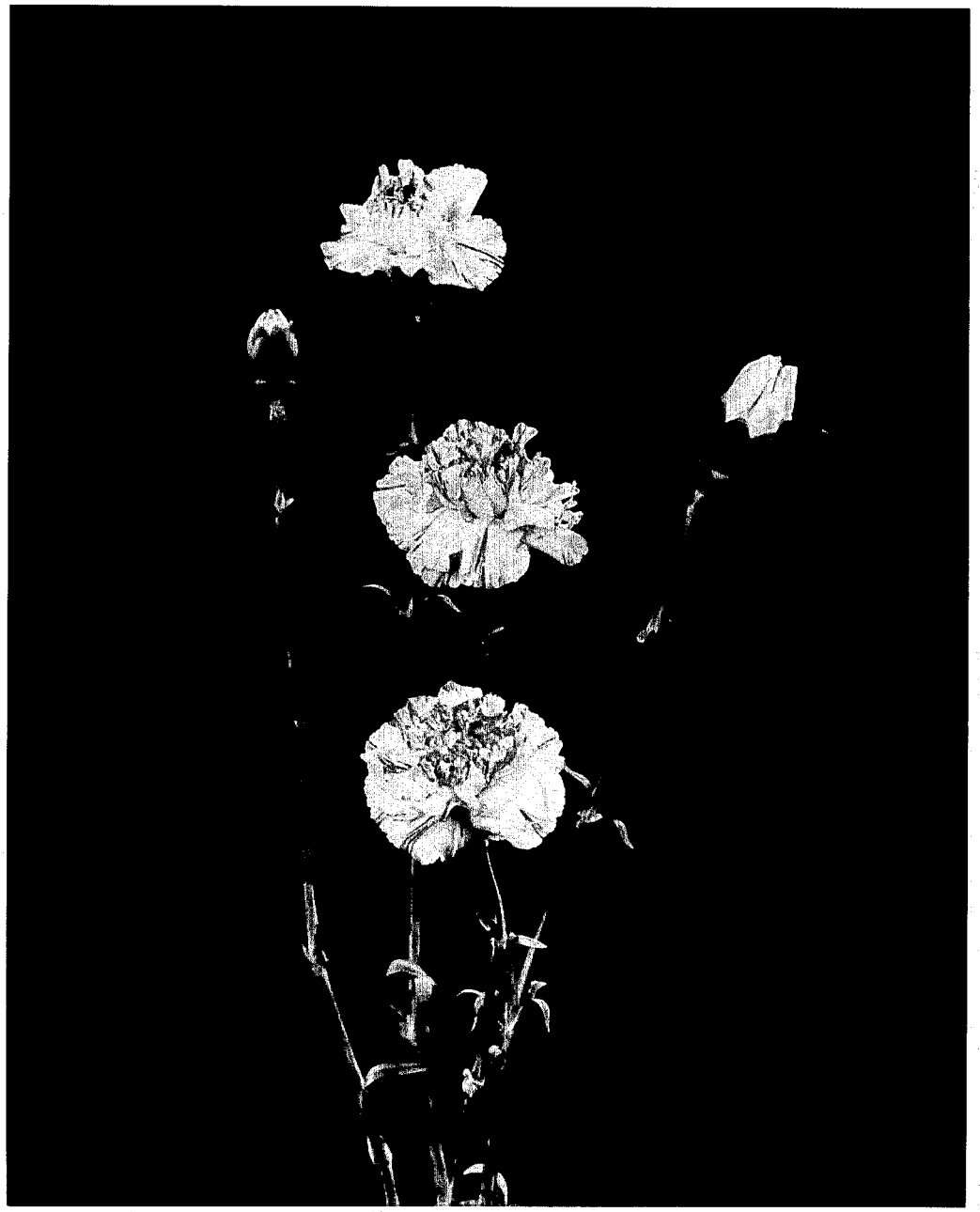

* * * * *